(12) United States Patent
Munar et al.

(10) Patent No.: US 8,053,189 B2
(45) Date of Patent: Nov. 8, 2011

(54) METHOD FOR THE DIAGNOSIS OF COLORECTAL CANCER

(75) Inventors: Gabriel Capella Munar, Madrid (ES); Daniel Azuara García, Madrid (ES)

(73) Assignee: Fina Biotech, S.L.U. (ES)

( * ) Notice: Subject to any disclaimer, the term of this patent is extended or adjusted under 35 U.S.C. 154(b) by 100 days.

(21) Appl. No.: 12/264,024

(22) Filed: Nov. 3, 2008

(65) Prior Publication Data

US 2010/0112555 A1 May 6, 2010

(51) Int. Cl.
*C12Q 1/68* (2006.01)
*C12P 19/34* (2006.01)
*C07H 21/02* (2006.01)
*C07H 21/04* (2006.01)

(52) U.S. Cl. ............... 435/6.11; 435/6.14; 435/6.17; 435/6.18; 536/23.5; 536/24.1

(58) Field of Classification Search .................... None
See application file for complete search history.

(56) References Cited

U.S. PATENT DOCUMENTS

| 2004/0053304 | A1 | 3/2004 | Markowitz |
| 2009/0111120 | A1* | 4/2009 | Meltzer et al. ............. 435/6 |
| 2009/0215709 | A1* | 8/2009 | Van Criekinge et al. ....... 514/34 |

FOREIGN PATENT DOCUMENTS

| WO | 2004086949 | 10/2004 |
| WO | 2005001140 | 1/2005 |
| WO | 2005003381 | 1/2005 |
| WO | 2006002344 | 1/2006 |
| WO | WO 2006/088940 | * 8/2006 |

OTHER PUBLICATIONS

Ehrlich et al. Oncogene 2002. 21: 5400-5413.*
Ushijima et al. Nature Reviews. 2005. 5: 223-231.*
Tang et al. International Journal of Cancer. 2006. 119: 2603-2606; published online Sep. 21, 2006.*
Goel et al. Gastroenterology. Jan. 2007. 132(1): 127-138.*
Wojdacz et al. Nucleic Acids Research. Feb. 2007. 35: e41, pp. 1-7.*
Ogino et al. Gut 2006. 55: 1000-1006.*
Konstanze Lenhard, et al., "Analysis of Promoter Methylation in Stool: A Novel Method for the Detection of Colorectal Cancer", Clinical Gastroentrology and Hepatology, 2005, vol. 3, pp. 142-149.
David A. Ahlquist, et al., "Colorectal Cancer Screening by Detection of Altered Human DNA in Stool: Feasibility of a Multitarget Assay Pane", Gastroebterology, 2000, vol. 119, pp. 1219-1227.
David A. Ahlquist, "Stool-Based DNA Tests for Colorectal Cancer: Clinical Potential and Early Results", Reviews in Gastroenterological Disorders, 2002, vol. 2, pp. s20-s26.
David A. Ahlquist, et al., "Stool screening for colorectal cancer: evolution from occult blood to molecular markers", Clinica Chimica Acta 315, 2002, pp. 157-168.
Nigel J.Belshaw, et al., Use of DNA from Human Stools to Detect Aberrant CpG Island Methylation of Genes Implicated in Colorectal Cancer?, Cancer Epidemiol Biomarkers Prev, 2004, vol. 13, No. 9. pp. 1495-1501.

Dean E. Brenner, et al., "Fecal DNA Biomarkers for the detection of Colorectal Neoplasia: Attractive but Is IT Feasible", Journal of the National Cancer Institute, vol. 97, No. 15, Aug. 3, 2005, pp. 1107-1109.
Gabriel Capella, "Is fecal DNA testing superior to fecal occult-blood testing for colorectal cancer screening?" Nature Clinical Practice, May 2005, vol. 2, No. 5, pp. 234-235.
Seung Myung Dong, et al., "Detecting Colorectal Cancer in Stool With the Use of Multiple Genetic Targets", Journal of the National Cancer Institute, Jun. 2001, vol. 93, No. 11, pp. 858-865.
Susumu Eguchi, et al., "Mutations of the P53 Gene in the Stool of Patients with Resectable Colorectal Cancer", Presented at the Seventh Annual Meeting of the Japanese Research Society for Gastroenterological Carcinogensis, Oita, Japan, Sep. 8-9, 1995.
James G. Herman, et al., "Methylation-specific PCR: A novel PCR assay for methylation status of CPG islands", Proc. Natl. Acad. Sci. USA, vol. 93. pp. 9821-9826, Sep. 1996.
Manel Esteller. et al., "Epigenetic inactivation of LKB1 in primary tumors associated with the Peutz-Jeghers syndrome", Onogene, 2000, vol. 19, pp. 164-168.
Manel Esteller, "Epigenetics in Cancer", New England Journal of Medicine, 2008, vo. 358, pp. 1148-1159.
Manel Esteller, et al., "A Gene Hypermethylation Profile of Human Cancer", Perspectives in Cancer Research, vol. 61, pp. 3225-3229,Apr. 15, 2001.
Manel Esteller, et al., Analysis of Adenomatous Polyposis Coli Promoter Hypermethylation in Human Cancer, Cancer Research 60, pp. 4366-4371, Aug. 15, 2001.
Manel Esteller, et al., "DNA methylation patterns in hereditary human cancers mimic sporadic tumorigenesis", Human Molecular Genetics, 2001, vol. 10, No. 26, pp. 3001-3007.
Manel Esteller, et al., "Hypermethylation-associated Inactivation of the Cellular Retinol-Binding-Protein 1 Gene in Human Cancer", Cancer Research 62, Oct. 15, 2002, pp. 5902-5905.
Jordi Frigola, et al., "Epigenetic remodeling in colorectal cancer results in coordinate gene suppression across and entire chromosome band", Nature Genetics, vol. 38, No. 5, May 2006, pp. 540-549.
James G. Herman, et al., "Incidence and functional consequences of hMLH1 promoter hypermethylation in colorectal carcinoma", Proc. Natl. Acad. Sci. USA, vol. 95. pp. 6870-6875, Jun. 1998.
Helen M. Sheilds, et al., "Factors That Influence the Decision to Do an Adequate Evaluation of a Patient with a Positive Stool for Occult Blood", The American Journal of Gastroenterology, vol. 96, No. 1, 2001, pp. 196-201.
Kenneth Song, et al, "Fecal DNA Testing Compared With Conventional Colorectal Cancer Screening Methods: A Decision Analysis", Gastroenterology 2004, vol. 126, pp. 1270-1279.

(Continued)

*Primary Examiner* — Carla Myers
(74) *Attorney, Agent, or Firm* — Cantor Colburn LLP (57) ABSTRACT

The object of the present invention refers to an in vitro method for diagnosing colorectal cancer based on the determination from a biological sample obtained from a subject, of promoter methylation status of at least one of the genes APC, RARB2 and p14 and, optionally, MGMT and p16. Likewise, object of the present invention is a kit for performing the method of the invention.

4 Claims, 2 Drawing Sheets

OTHER PUBLICATIONS

Giovanni Traverso, et al., "Detection of APC Mutations in Fecal DNA From Patients With Colorectal Tumors", New England Journal of Medicine, vol. 346, No. 5, pp. 311-320.

Giovanni Traverso, et al., "Detection of proximal colorectal cancers through analysis of faecal DNA", The Lancet, vol. 359, (2002), pp. 403-404.

Duncan Whitney, et al., "Enhanced Retrieval of DNA from Human Fecal Samples in Improved Performance of Colorectal Cancer Screening Test", Journal of Molecular Diagnostics, vol. 6, No. 4, Nov. 2004, pp. 386-395.

Sidney Winawer, et al. "Colorectal Cancer Screening and Surveillance: Clinical Guidelines and Rational-Update Based on New Evidence", American Gastroenterological Association Gastroenterology, 2003, vol. 124, pp. 544-560.

Hong Zou, et al, "Highly Methylated Genes in Colorectal Neoplasia: Implications for Screening", Cancer Epidemiol Biomarkers Prev., Dec. 2007, vol. 16, No. 12. pp. 2686-2696.

Marion Zitt, et al., "DNA methylation in colorectal cancer-Impact on screening and therapy monitoring modalities?", Disease Markers 23, (2007) pp. 51-71.

Hong-Zhi Zou, et al., "Detection of Aberrant p16 Methylaytion in the Serum of Colorectal Cancer Patients", Clinical Cancer Research, vol. 8, Jan. 2002, pp. 188-191.

Hannes M. Muller, "Methylation changes in faecal DNA: a marker for colorectal cancer screening", The Lancet, vol. 363, Apr. 17, 2004, pp. 1283-1285.

Thomas F. Imperiale, et al., "Risk of Advanced Proximal Neoplasms in Asymptomatic Adults According to The Distal Colorctal Findings", The New England Journal of Medicine, vol. 343, No. 3, Jul. 2000, pp. 169-174.

Thomas F. Imperiale, et al., "Fecal DNA versus Fecal Occult Blood for Colorectal-Cancer Screening in an Average-Risk Population", New England Journal of Medicine, vol. 351, No. 26, Dec. 23, 2004, pp. 2704-2714.

Lasse S. Kristensen, et al., "Sensitive Melting Analysis after Real Time-Methylation Specific PCR (SMART-MSP): high-throughput and probe-free quantitative DNA methylation detection", Nucleic Acids Research, 2008, vol. 36, No. 7.

Wai K. Leung, et al., "Detection of Hypermethylated DNA or Cyclooxygenase-2 Messanger RNA in Fecal Samples of Patients with Colorectal Cancer or Polyps", American Journal of Gastroenterology, 2007, vol. 102, pp. 1070-1076.

Wai K. Leung, et al., "Quantitative Detection of Promoter Hypermethylation in Multiple Genesd in the Serum of Patients with Colorectal Cancer", American Journal of Gastroenterology, 2005, vol. 100, pp. 2274-2279.

Wai K. Leung, et al., "Detection of Epigenetic Changes in Fecal DNA as a Molecular Screening for Colorectal Cancer: A Feasible Study", Clinical Chemistry 50, No. 11, 2004, pp. 2179-2182.

David A. Lieberman, et al., "Use of Colonoscopy to Screen Asymptomatic Adults for Colorectal Cancer", The New England Journal of Medicine, vol. 343, No. 3, Jul. 20, 2000, pp. 162-168.

Alexandre Loktionov, et al., "Quantitation of DNA from Exfoliated Colonocytes Isolated from Human Stool Surface as a Novel Noninvasive Screening Test Colorectal Cancer", Clinical Cancer Research, vol. 4, Feb. 1998, pp. 337-342.

Jack S. Mandel, et al., "The Effect of Fecal Occult-Blood Screening on the Incidence of Colorectal Cancer", The New England Journal of Medicine, vol. 343, No. 22, Nov. 30, 2000, pp. 1603-1607.

Thomas Mikeska, et al., "Optimization of Quantitative MGMT Promoter Methylation Analysis Using Pyrosequencing and Combined Bisulfite Restriction Analysis", Journal of Molecular Diagnostics, vol. 9, No. 3, Jul. 2007, pp. 368-381.

Pere Puig, et al., "A Highly Sensitive Method for K-ras Mutation Detection is Useful in Diagnosis of Gastrointestinal Cancer", Int. J. Cancer, vol. 85, (2000) pp. 73-77.

David Sidransky, et al., "Identification of ras Oncogene Mutations in the Stool of Pateints with Curable Colorectal Tumors", Science, vol. 256, Apr. 3, 1992, pp. 102-105.

Goro Nakayama, et al., "p16 Methylation in Serum as a Potential Marker for the Malignancy of Colorectal Carcinoma", Anticancer Research 27, (2007), pp. 3367-3370.

Susan Cottrell, et al., "Sensitive Detection of DNA Methylation," Ann, N.Y. Acad. Sci. 983: 120-130, (2003).

L. Ore, "Screening with faecal occult blood test (FOBT) for colorectal cancer: assessment of two methods that attempt to improve compliance", European Journal of Cancer Prevention, vol. 10, 2001, pp. 251-256.

Neal K. Osborn, "Stool Screening for Colorectal Cancer: Molecular Approaches", Gastroenterology 2005, vol. 128, pp. 192-206.

Pere Puig, et al., "Improved Detection of K-ras Codon 12 Mutations in Fecal Exfoliated Cells", Laboratory Investigation, vol. 79, No. 5, pp. 617-618, May 2009.

Zsolt Petko, et al., "Aberrantly Methylated CDKN2A, MGMT, and MLH1 in Colon Polyps and in Fecal DNA drom Patients with Colorectal Polyps", Clinical Cancer Research, vol. 11. Feb. 1, 2005, pp. 1203-1209.

\* cited by examiner

SEQUENCE LISTING

```
<160> NUMBER OF SEQ ID NOS: 5

<210> SEQ ID NO 1
<211> LENGTH: 40
<212> TYPE: DNA
<213> ORGANISM: Artificial
<220> FEATURE:
<223> OTHER INFORMATION: Primer 5'-3' RARB2

<400> SEQUENCE: 1
tttaaagtgt gggttggggg cccaacaacc ctacaaaaac                     40

<210> SEQ ID NO 2
<211> LENGTH: 41
<212> TYPE: DNA
<213> ORGANISM: Artificial
<220> FEATURE:
<223> OTHER INFORMATION: Primer 5'-3' p16

<400> SEQUENCE: 2
gttggttatt agagggtggg gctacaaacc ctctacccac c                   41

<210> SEQ ID NO 3
<211> LENGTH: 38
<212> TYPE: DNA
<213> ORGANISM: Artificial
<220> FEATURE:
<223> OTHER INFORMATION: Primer 5'-3' MGMT

<400> SEQUENCE: 3
```

```
ggatatgttg ggatagttaa ataaataaaa atcaaaac                                   38

<210> SEQ ID NO 4
<211> LENGTH: 44
<212> TYPE: DNA
<213> ORGANISM: Artificial
<220> FEATURE:
<223> OTHER INFORMATION: Primer 5'-3' p14

<400> SEQUENCE: 4
gtttattttt ggtgttaaag ggctaactcc tcaataacat caac                            44

<210> SEQ ID NO 5
<211> LENGTH: 38
<212> TYPE: DNA
<213> ORGANISM: Artificial
<220> FEATURE:
<223> OTHER INFORMATION: Primer 5'-3' APC

<400> SEQUENCE: 5
ggttagggtt aggtaggttg ctacaccaat acaaccac                                   38
```

METHOD FOR THE DIAGNOSIS OF COLORECTAL CANCER

FIELD OF THE INVENTION

The field of application of the present invention is the medical sector, in the field of Molecular Biology. More specifically, the invention addresses a method for the early diagnosis of colorectal cancer and the kit for performing the method.

BACKGROUND OF THE INVENTION

Colorectal cancer (CRC) is the third most common form of cancer and the second leading cause of cancer-related deaths in the western world. Its natural evolution (adenoma-carcinoma sequence is believed to occur in most patients) and accessibility by non-surgical methods makes it suitable for early detection and prevention.

Early detection greatly improves the chances of curing CRC. Colonoscopy is an extremely specific and sensitive test, which could be considered the reference method for an early diagnosis of CRC [44,45], and is typically recommended to be performed at 10-year intervals for detection, usually beginning at the age of 50 [1]. However, it is an invasive test which requires good bowel preparation and the patient's cooperation. It is also associated to a minor risk of serious complications, reducing its generalised use.

Fecal occult blood testing (FOBT) is generally considered to be the best non-invasive test for CRC, since it reduces cancer-related mortality when used programmatically [2]. However, its sensitivity is fairly low (15% for adenomas and 35% for carcinomas), implying that a substantial proportion of colorectal neoplasms are missed [1]. Additionally, it has a low specificity giving rise to a lot of false positives. Also, some tests require patients to change their diet, which considerably reduces its usability [46-47].

In this context, DNA testing in non-invasive samples appears as a feasible approach that can complement and probably outperform other screening test for CRC [3-5] [23-26], although to date, its routine clinical application is still a matter of debate [6-7, 27].

DNA appears to be stable in stool, and although PCR inhibitors are present, purification steps have made it possible to carry out PCR-based analyses systematically in a high proportion of samples [28-30]. This proportion is even higher when lesions, especially colorectal carcinomas, are diagnosed. Stool samples in subjects with CRC can contain more exfoliated cells and/or amplifiable DNA [31].

Most of the studies published to date using stool DNA have detected mutations in single genes or markers (e.g., K-ras, p53, APC or BAT26) [16,26,32-33] with acceptable although variable sensitivity and specificity. Others have postulated the use of a multiple target mutation assay panel, which in a large screening setting, showed a sensitivity of 51.6% for carcinomas and 32.5% for adenomas with high grade dysplasia [29]. These promising results are associated with a moderate reduction in the level of specificity (95%), due to the detection of mutations in endoscopically normal colons.

Methylation of the cytosine residues of CpG-rich sequences (CpG islands), located within the gene promoter regions, is usually associated with gene silencing and is considered as a mechanism for cancer gene inactivation.

The genomes of pre-neoplastic, cancerous and aged cells share three important changes in the methylation levels, as early events in the development of certain tumours. Firstly, the hypomethylation of heterochromatin which leads to genomic instability and increases the events of mitotic recombination; secondly, hypermethylation of individual genes, and finally, hypermethylation of the CpG islands of constitutive genes and tumour suppressant genes. The two levels of methylation can occur individually or simultaneously. In general, hypermethylation is involved in gene silencing and hypomethylation in the over-expression of certain proteins linked to the processes of invasion and metastasis.

Promoter hypermethylation of many genes, such as $p16^{INK4a}$, $p14^{ARF}$, APC, MGMT, LKB1, hMLH1, RASSF1A, CRBP1, RARB2 [8-10], are a common and early events in colorectal tumorigenesis.

In the last few years, changes in the methylation of cytosine residues of CpG-rich sequences (CpG islands) have been increasingly recognised as very common molecular aberrations presumed to be of clinical use [34]. In colorectal cancer, methylated markers are interesting for screening because they occur with high frequency in early stage neoplasia [35]. Detection of CpG islands methylation in human DNA isolated from stool [11-12,36] or serum [37-39] has been proposed as a novel strategy for the early diagnosis of colorectal neoplasia. Thus, the methylation status of the gene promoter regions such as p16, MGMT, MLH1, SFRP2, HIC1 and vimentine in stool DNA has been evaluated, either individually or using a combined panel [11-15,25,40, 48-53]. To date, the methylation of SFRP2 is the most sensitive individual marker (sensitivity of 77-90%). However, both individual and combined methylated markers have been hampered by a relatively high proportion of false positives.

Assesment of promoter hypermethylation in stool DNA could provide a valuable approach to the non-invasively screening for early colorectal lesions [11-15]. Notwithstanding, the lack of specificity demonstrated until now made its potential clinical use difficult. The DNA resulting from the exfoliation of the colonic epithelium in the faecal matter is difficult to amplify given the enormous number of PCR inhibitors found in stools.

Based on the current needs and difficulties in establishing a non invasive early diagnosis of colorectal cancer with acceptable sensitivity and specificity, the authors of the invention have developed a panel of biomarkers of methylation in stool suitable for routine use in clinical practice.

Thus, following considerable research, the authors have found a panel of 5 methylated markers (RARB2, MGMT, $p16^{INK4a}$, APC and $p14^{ARF}$) which jointly represent most tumours.

After finding these five markers, the authors of the invention, have developed a new method for the early diagnosis of colorectal cancer based on the analysis of the melting curves through real-time PCR detection (RT PCR Melting curve, MC) of the state of methylation of the promoters of the 5 genes: RARB2, $p16^{INK4a}$, MGMT, $p14^{ARF}$ and APC in stool DNA, demonstrating high sensitivity in the early detection of CRC tumours and excellent specificity (no false positives in normal colonoscopies).

This new method allows the non invasive detection of pre-malignant and malignant neoplastic alterations of the colon with high sensitivity and excellent specificity, allowing its routine use in clinical practice.

BRIEF DESCRIPTION OF THE DRAWINGS

FIG. 2 shows the prevalence of methylation in the different markers analysed in the study in the stool DNA (a) and in the tissue (b) in the validation set.

OBJECT OF THE INVENTION

The object of the present invention refers to an in vitro method for the diagnosis of colorectal cancer based on the determination from a biological sample obtained from a subject, of the promoter methylation status of at least one of the genes APC, RARB2 and p14 and, optionally, MGMT and p16.

Likewise, the object of the present invention is a kit for carrying out the method of the invention.

DESCRIPTION OF THE INVENTION

A main aspect of the invention contemplates an in vitro method for the diagnosis of colorectal cancer comprising a) obtaining a biological sample from a subject; and b) determining from the biological sample the methylation status of the promoter of at least one of the following genes: APC, RARB2 and p14, wherein the methylation of the promoter region of said genes is indicative of said disease.

In the present invention, the term "subject" refers to a human being.

In a particular embodiment, the method comprises additionally determining the methylation status of the promoter of at least a gene selected from p16 and MGMT.

The APC gene (adenomatous polyposis coli) (also known as GS; DP2; DP3; BTPS2; DP2.5), located in 5q21-q22, access number NCBI M74088.1, codifies a tumor suppressant protein that acts as an antagonist to the Wnt signalling route. It is also involved in other processes such as cellular migration and adhesion, transcriptional activation and apoptosis. Its deactivation is considered an alteration present in the vast majority of colorectal tumours.

The RARB gene (Retinoic acid receptor Beta) (also known as HAP, NR1 B2, RRB2), located in 3p24, access number NCBI Y00291.1 codifies a protein belonging to the superfamily of thyroid/steroid hormone receptors of nuclear transcriptional regulators. The gene expresses itself using two different promoters, which have different CpG islands. RARB1 expresses itself mainly during embryogenesis, whereas RARB2 expresses itself in adult tissue and is hypermethylated in carcinogenic cells.

The p16 gene (cyclin-dependent kinase inhibitor 2A) (CDKN2A), access number L27211.1, is a tumour suppressant gene. Therefore, mutations in this gene increase the risk of developing a wide variety of types of cancer, mostly melanoma. The p16 gene has an alternative reading frame (ARF) which codifies the protein p14arf, involved in stabilising p53, and positively regulated by E2F. Both genes are involved in regulating the cell cycle.

The gene MGMT (O-6-methylguanine-DNA methyltransferase) is located in 10q26, access number NCBI M29971.1. This gene codifies a protein whose function is to repair DNA lesions, basically in the area of guanine.

In a preferred embodiment, the diagnosis method is based on simultaneous determination of the promoter methylation status of APC, RARB2, p16, MGMT and p14 genes.

The biological sample for analysis, previously isolated from the subject, may be a blood or stool sample. Preferably, stools are used.

In order to determine promoter methylation status of of the marker genes, the DNA is extracted from the isolated sample.

In a particular embodiment, following the stool extraction, observing a specific protocol (17), the methylation status of the specified markers is analysed.

Determining the methylation status of the promoters of the 5 genes can be carried out using various techniques.

Methylation-specific PCR (MSP) is a widely used PCR-based technique which selects as a target the methylation status of a limited number of CpG residues with a high sensitivity. However, in line with the previously noted results [41-43], false positives can be observed in both endoscopically normal colons and in patients with inflammatory bowel disease (IBD). The incomplete conversion following treatment with bisulphite of the CpG in unmethylated samples, in addition to the warping of the amplified alleles and the high analytical sensitivity of the technique, are the reasons behind the appearance of false positives in the results.

On the basis of these limitations, preferably in the present invention methylation is determined by analysing the melting curve (MC). Analysis of the MC of the promoter regions detect simultaneously all CpG residues within an amplified region.

Due to the cytosine-guanine (CG) content following treatment of the sample with sodium bisulphite, those that are methylated will present a higher melting temperature (CG bases join with 3 hydrogen bridge linkages while the adenine-thymine bases (AT) join with 2). This makes it possible to establish for each marker indicative temperatures of whether the sample is methylated or not.

Using the MC technology, the assessment of the panel of methylation markers in the stool DNA identifies pre-malignant and malignant growths with high sensitivity and excellent specificity.

Another main aspect of the invention contemplates a colorectal cancer diagnosis kit for performing the diagnosis method that is the object of this invention. The kit comprises a set of primers (Table 1) suitable for determining in a biological sample the methylation status of the promoter of at least one of the genes APC, RARB2 and p14. In addition, the kit can include primers for determining the state of methylation of the promoter of at least one of the genes p16 and MGMT.

Preferably, the Kit comprises of a set of primers suitable for determining simultaneously the promoter methylation status of the APC, RARB2, p14, MGMT and p16 genes.

EXAMPLES

Materials and Methods
Patients and Collecting of Fecal and Tissue Samples
Tumor Tissue Analyses A set of biopsies of 250 primary colorectal tumours and paired normal samples were used to evaluate the prevalence of the promoter methylation in 7 different genes (see below).

Initial set. Fecal samples were consecutively obtained following a laxative treatment administered to 12 patients recently diagnosed with primary colorectal carcinomas and 20 patients with adenomas prior to a colonoscopy, patients admitted to the Hospital de la Santa Creu i Sant Pau for a colonoscopy under the clinical suspicion of cancer. Paired biopsies of the lesions identified during the colonoscopy and stored as fresh frozen samples.

Validation set. Stool samples were collected from 28 patients with sporadic CRC, 23 patients with adenomas, 17 with inflammatory bowel disease (IBD) with colonic location (ulcerative colitis and Crohn colitis) and 20 macroscopically normal subjects undergoing surgery or endoscopy at the University Hospital of Bellvitge. Fecal samples from CRC patients were collected after laxative treatment prior to colonic surgery and during the colonoscopy (bowel lavage) from the remaining patients. Stools were stored at −80° C. until processed. All patients gave informed written consent to participate and for their biological samples to be analysed.

DNA Isolation and Bisulphite Modification

All tissue and stool samples were coded before storage, so that laboratory personnel were not aware of the patients' clinical diagnosis. DNA was extracted from the tissue or cell matter obtained after centrifugation of the bowel lavage or solid stools, as previously described [16-17]. One μg of DNA was chemically modified to convert all non-methylated cytosine to uracil using the EZ DNA methylation-gold kit (Zymo Research, Orange, Calif.) and eluted in 30 μL of elution buffer. DNA from normal lymphocytes treated in vitro with SssI methyltransferase (New England Biolabs Inc., Beverly, Mass.) was used as a positive control of the methylated alleles, whereas DNA from normal lymphocytes was used as control for unmethylated alleles.

DNA Methylation Analysis
Methylation-Specific PCR (MSP)

Promoter methylation was studied in RARB2, $p16^{INK4a}$, MGMT, $p14^{AFR}$, APC, hMLH1 and LKB1 by using MSP, a method that distinguishes methylated from unmethylated alleles of a given gene [18]. Following the DNA's treatment with bisulphite, which converts the unmethylated cytosines, but not the methylated ones, to uracil, DNA was amplified by PCR using specific primers to methylated and unmethylated sequences. The primers and the PCR conditions for the MSP analysis have been previously described for RARB2, $p16^{INK4a}$, MGMT, $p14^{ARF}$, APC, hMLH1 and LKB [8-9,19-21].

Real Time PCR Temperature Dissociation (Melting Curves)

Figure 1:
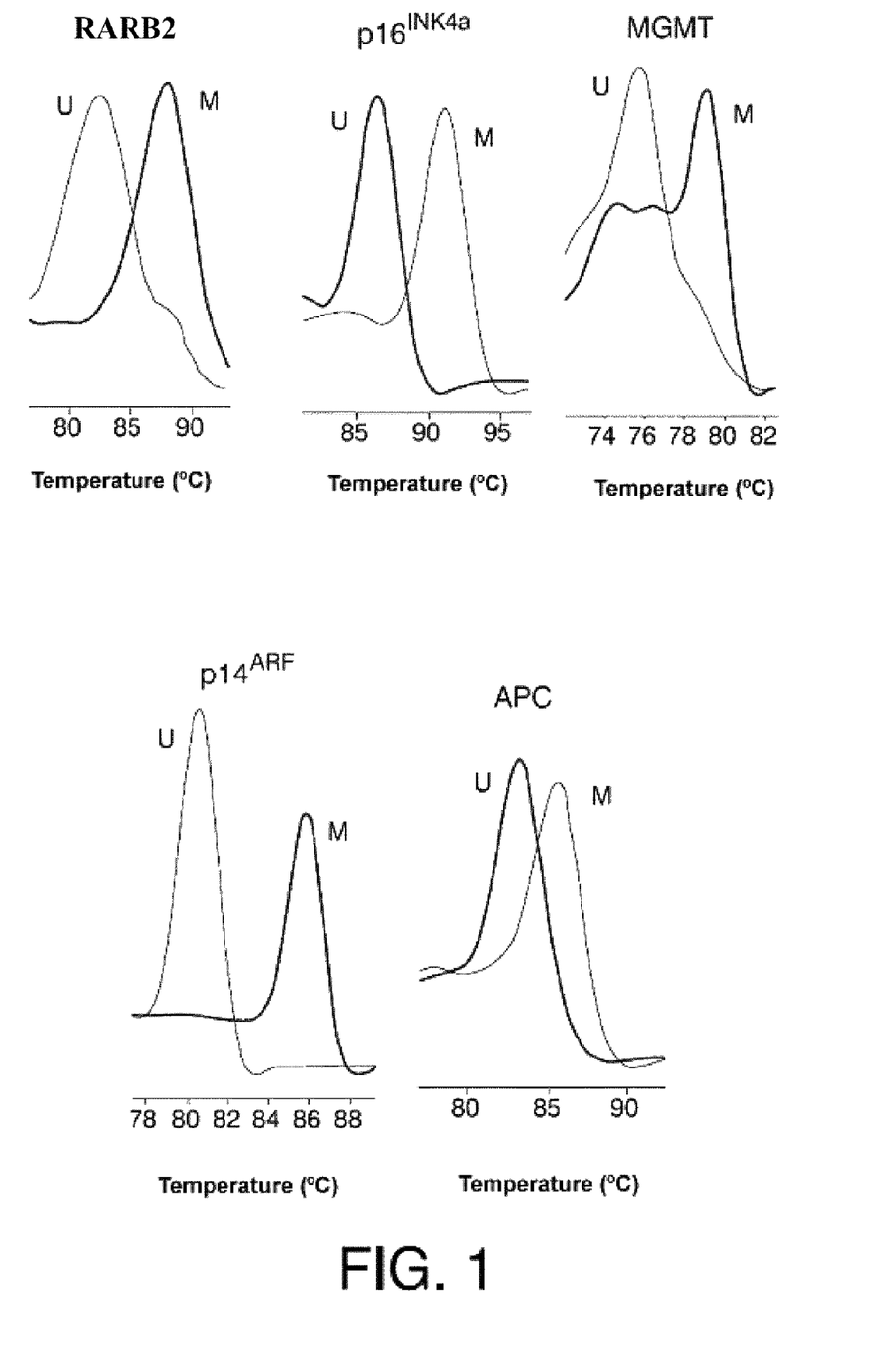
FIG. 1 shows the different melting temperatures according to the markers and according to the state of methylation of the sample (M: methylated; U: unmethylated).

The presence of methylated DNA was detected on the basis of the melting temperature by RT PCR. We analysed the methylation status of 5 genes (RARB2, $p16^{INK4a}$, MGMT, $p14^{ARF}$ and APC) (FIG. 1). A PCR was made in all cases in order to obtain a fragment of each one of the CpG islands for analysis (see the conditions in table 1) using a Light Cycler®2.0 (Roche Applied Science) and the Fast Start DNA Master Sybr Green I mix (Roche Applied Science) with real time detection, as described [22].

TABLE 1

Sequence of the primers, size of the products, ringing temperature and internal CpGs for the MC tests.

| Gene | Sequence 5'-3' of the primer | Product size (pb) | Annealing temperature (° C.) | Internal CpGs |
|---|---|---|---|---|
| RARB2 | SEQ ID NO 1 | 273 | 60 | 18 |
| $p16^{INK4a}$ | SEQ ID NO 2 | 254 | 62 | 28 |
| MGMT | SEQ ID NO 3 | 216 | 60 | 22 |
| $p14^{ARF}$ | SEQ ID NO 4 | 224 | 64 | 26 |
| APC | SEQ ID NO 5 | 192 | 62 | 16 |

After bisulphite treatment, a methylated sequence conserves the CG pairs whereas an unmethylated sequence presents changes to TG pairs. This change in the CG content gives as a result, a variation in the melting temperature of a particular DNA fragment. Based on the melting temperatures in respect of a series of controls, whose state of methylation was known beforehand, it was possible to assign a state of methylation to the samples undergoing testing. The test of analysing the melting-methylation curve only required one set of primers, which did not include methylation susceptible CpG on its sequence, which increased the reliability of the reaction. This set of primers (table 1) amplified both the methylated and the unmethylated sequence after the treatment with bisulphite. The difference became evident from the melting curves, since the methylated product presented a higher melting temperature than that the unmethylated product.

RESULTS

Methylation in CRC Tumours by MSP

The prevalence of promoter hypermethylation in tumoral biopsies was as follows: RARB2 (54%, 135 of 250), $p16^{INK4a}$ (35%; 88 of 250), MGMT (35%, 88 of 250), $p14^{ARF}$ (30%, 75 of 50), APC (20%, 50 of 250), hMLH1 (15%, 38 of 250) and LKB1 (5%, 13 of 250). Informative results were obtained for all tumours when combining all markers analyzed. In 100 cases, paired normal mucosa was analysed, observing a low percentage of methylation: RARB2 (4%), MGMT (4%), $p16^{INK4a}$ (2%), hMLH1 (2%), $p14^{ARF}$ (1%), APC (0%) and LKB1 (0%). Finally, no methylation was detected in DNA extracted from the peripheral blood lymphocytes (PBLs) of healthy donors.

Training Set
Methylation in Tissue and Fecal DNA by MSP

Taking into account the five most prevalent markers were selected for analysing the stool DNA (RARB, p16, MGMT, p14 and APC). We found that 88% (28 of 32) of the primary tumours (10 of 12 carcinomas and 18 of 20 adenomas) were positive for at least one methylation marker (table 2). Most carcinomas (9 of 10) and a smaller proportion of adenomas (7 of 18) harbored three or more methylated markers. Promoter hypermethylation was found in 25 of 32 (78%) cases for RARB2, 18 of 32 (56%) for MGMT 18 of 32 (56%) cases for $p16^{INK4a}$, 13 of 32 (40%) for APC and 10 of 32 (31%) for $p14^{ARF}$, $p14^{ARF}$ and APC promoter hypermethylation only increased in carcinomas, when compared to adenomas.

Aberrant methylation of faecal DNA was detected in 1 or more markers in 9 of 12 (75%) carcinomas and in 12 of 20 adenomas (60%). This proportion varied among markers: 92% (12 of 13) for APC, 50% (9 of 18) for $p_{16}^{INK4a}$, 24% (6 of 25) for RARB2, 10% (1 of 10) for $p14^{ARF}$ and 11% (2 of 18) for MGMT. No aberrant methylation of promters was detected in DNA collected of the 4 tumours that do not present aberrant gene methylation. Sensitivity of the methylation markers for the detection of tumoural cells was 75% for carcinomas and 60% for adenomas (table 2).

TABLE 2

Prevalence of methylated markers in faecal and biopsy DNA in pairs in the initial group of samples (MSP results).

| | Faecal DNA | | | Tissue | |
|---|---|---|---|---|---|
| | n | ≧1 methylated gene | ≧2 methylated genes | n | ≧1 methylated gene | ≧2 methylated genes |
| Adenomas | 20 | 12(60%) | 5(25%) | 20 | 18(90%) | 14(70%) |
| Carcinomas | 12 | 9(75%) | 2(17%) | 12 | 10(83%) | 10(83%) |

Validation Set
Methylation in Tissue and Fecal DNA by Melting Curves

In the first instance, the biopsy and faecal DNA obtained from healthy volunteers and IBD patients was analysed through MSP. An abnormally high prevalence of aberrant methylation in IBD patients in addition to the identification of a large proportion of positive cases in healthy donors, led us to investigate the analysis of melting curves as an alternative to MSP. By means of this approach, at least one methylation marker was detected in 79% of the carcinoma biopsies (22 of 28) and in 70% of the adenomas (16 of 23) (table 3).

TABLE 3

Prevalence of methylated markers in faecal and biopsy DNA in pairs in the validation group (MC results).

|  | Faecal DNA | | | Tissue | | |
| --- | --- | --- | --- | --- | --- | --- |
|  | n | ≧1 methylated gene | ≧2 methylated genes | n | ≧1 methylated gene | ≧2 methylated genes |
| Normal | 20 | 0 | 0 | 20 | 0 | 0 |
| IBD | 17 | 2(12%) | 0 | 17 | 3(18%) | 0 |
| Adenomas | 23 | 9(42%) | 2(9%) | 23 | 16(70%) | 7(30%) |
| Carcinomas | 28 | 18(64%) | 7(25%) | 28 | 22(79%) | 9(32%) |

The prevalence for each marker, taking together adenomas and carcinomas, was as follows: 28 of 45 (62%) for RARB2, 10 of 51 (20%) for p14$^{ARF}$, 7 of 36 (19%) for APC, 7 of 35 (20%) for MGMT and 3 of 48 (6%) for p16$^{INK4a}$. Three of 12 biopsies (25%) obtained from patients with IBD were positive for RARB2 (FIG. 2b)). None of the normal biopsies were positive for any of the analysed markers (table 4).

Figure 2A:
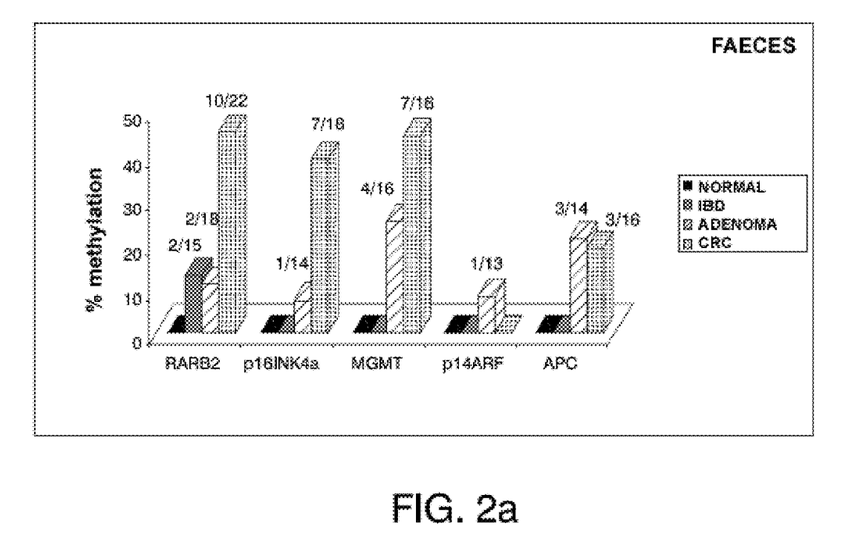
Figure 2B:
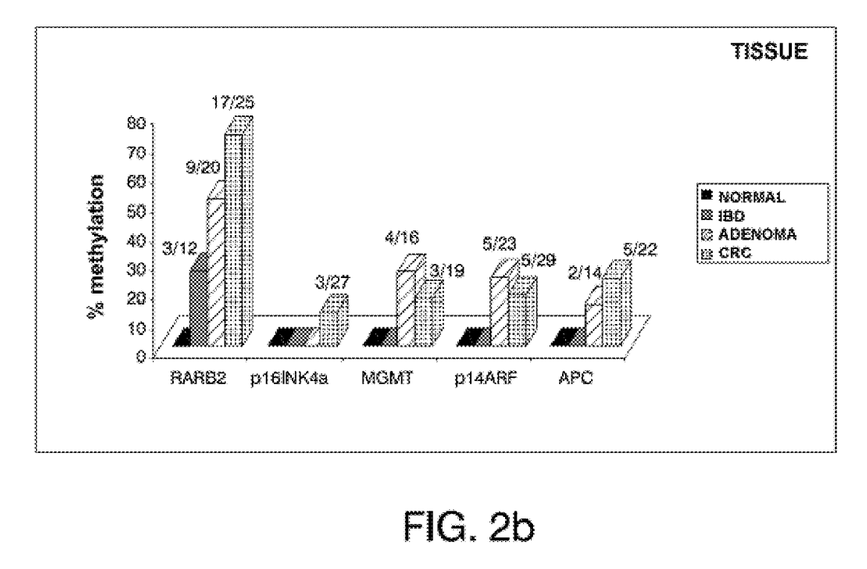

In respect of faecal DNA, aberrant methylation was detected in 64% of the carcinomas (18 of 28) and in 42% of the adenomas (9 of 23) (table 3), with the distribution of positive markers being as follows: 34% (11 of 32) for MGMT, 30% (12 of 40) for RARB2, 25% (8 of 32) for p16$^{INK4a}$, 20% (6 of 30) for APC and 3% (1 of 30) for p14$^{ARF}$. Once more, in 2 of 15 (13%) patients with IBD, RARB2 promoter hypermethylation was detected (FIG. 2a). No methylated marker was detected when the colonoscopy was normal (table 4).

TABLE 4

Prevalence of the 5 methylated markers in faecal and biopsy DNA in pairs, in the validation group (MC results).

|  | SAMPLE | p14 | p16 | RARB2 | APC | MGMT |
| --- | --- | --- | --- | --- | --- | --- |
| NORMAL | FAECES | 0% | 0% | 0% | 0% | 0% |
|  | TISSUE | 0% | 0% | 0% | 0% | 0% |
| INFLAMMATORY | FAECES | 0% | 0% | 2/15(13%) | 0% | 0% |
|  | TISSUE | 0% | 0% | 3/12(25%) | 0% | 0% |
| AD + T | FAECES | 1/30(3%) | 8/32(25%) | 12/40(30%) | 6/30(20%) | 11/32(34%) |
|  | PATHL. TISSUE | 10/51(20%) | 3/48(6%) | 28/45(62%) | 7/36(19%) | 7/35(20) |

The amplification for each marker in healthy individuals was as follows: 15 of 16 (94%) for MGMT 13 of 16 (81%) for RARB2, 15 of 20 (75%) for APC, 12 of 20 (60%) for p16$^{INK4a}$ and 8 of 20 (40%) for p14$^{ARF}$ (table 5).

TABLE 5

Amplification of the 5 markers in healthy individuals

|  | SAMPLE | p14 | p16 | RARB2 | APC | MGMT |
| --- | --- | --- | --- | --- | --- | --- |
| NORMAL | FAECES | 8/20(40%) | 12/20(60%) | 13/16(81%) | 15/20(75%) | 15/16(94%) |
| N = 20 | TISSUE | 20/20(100%) | 20/20(100%) | 15/16(94%) | 15/15(100%) | 15/16(94%) |
| INFLAMMATORY | FAECES | 13/17(76%) | 11/15(73%) | 15/17(88%) | 7/11(64%) | 12/15(80%) |
| N = 18 | TISSUE | 15/18(100%) | 13/14(93%) | 12/13(92%) | 12/13(92%) | 9/10(90%) |
|  | FAECES | 13/23(57%) | 14/23(61%) | 18/18(100%) | 14/19(74%) | 16/17(94%) |
| ADENOMA | TISSUE N | 22/23(96%) | 23/23(100%) | 21/21(100%) | 13/14(92%) | 18/18(100%) |
| N = 23 | TISSUE AD | 23/23(100%) | 21/23(91%) | 20/20(100%) | 14/16(88%) | 16/16(100%) |
|  | FAECES | 17/30(57%) | 18/30(60%) | 22/23(96%) | 16/21(76%) | 16/21(76%) |
| TUMOUR | TISSUE N | 27/28(96%) | 28/29(97%) | 23/25(92%) | 23/25(92%) | 24/25(96%) |
| N = 30 | TISSUE T | 29/30(97%) | 29/30(97%) | 26/27(96%) | 22/25(88%) | 21/21(100%) |

BIBLIOGRAPHY

1. Winawer S, Fletcher R, Rex D, et al. Colorectal cancer screening and surveillance: clinical guidelines and rationale-Update based on new evidence. *Gastroenterology* 2003; 124:544-60.
2. Mandel J S, Church T R, Bond J H, et al. The effect of faecaloccult-blood screening on the incidence of colorectal cancer. *The New England journal of medicine* 2000; 343:1603-7.
3. Dong S M, Traverso G, Johnson C, et al. Detecting colorectal cancer in stool with the use of multiple genetic targets. *J Natl Cancer Inst* 2001; 93:858-65.
4. Ahlquist D A. Stool-based DNA tests for colorectal cancer: clinical potential and early results. *Rev Gastroenterol Disord* 2002; 2 Suppl 1:S20-6.
5. Traverso G, Shuber A, Levin B, et al. Detection of APC mutations in faecalDNA from patients with colorectal tumors. *N Engl J Med* 2002; 346:311-20.
6. Brenner D E, Rennert G. FaecalDNA biomarkers for the detection of colorectal neoplasia: attractive, but is it feasible? *J Natl Cancer Inst* 2005; 97:1107-9.
7. Capella G. Is faecalDNA testing superior to faecaloccult-blood testing for colorectal cancer screening? *Nat Clin Pract Oncol* 2005; 2:234-5.
8. Esteller M, Fraga M F, Guo M, et al. DNA methylation patterns in hereditary human cancers mimic sporadic tumorigenesis. *Human molecular genetics* 2001; 10:3001-7.
9. Esteller M, Corn P G, Baylin S B, et al. A gene hypermethylation profile of human cancer. *Cancer research* 2001; 61:3225-9.
10. Esteller M, Guo M, Moreno V, et al. Hypermethylation-associated Inactivation of the Cellular Retinol-Binding-Protein 1 Gene in Human Cancer. *Cancer research* 2002; 62:5902-5.
11. Belshaw N J, Elliott G O, Williams E A, et al. Use of DNA from human stools to detect aberrant CpG island methylation of genes implicated in colorectal cancer. *Cancer Epidemiol Biomarkers Prev* 2004; 13:1495-501.
12. Leung W K, To K F, Man E P, et al. Detection of epigenetic changes in faecalDNA as a molecular screening test for colorectal cancer: a feasibility study. *Clinical chemistry* 2004; 50:2179-82.
13. Muller H M, Oberwalder M, Fiegl H, et al. Methylation changes in faecal DNA: a marker for colorectal cancer screening? *Lancet* 2004; 363:1283-5.
14. Petko Z, Ghiassi M, Shuber A, et al. Aberrantly methylated CDKN2A, MGMT, and MLH1 in colon polyps and in faecalDNA from patients with colorectal polyps. *Clin Cancer Res* 2005; 11:1203-9.
15. Lenhard K, Bommer G T, Asutay S, et al. Analysis of promoter methylation in stool: a novel method for the detection of colorectal cancer. *Clin Gastroenterol Hepatol* 2005; 3:142-9.
16. Puig P, Urgell E, Capella G, et al. A highly sensitive method for K-ras mutation detection is useful in diagnosis of gastrointestinal cancer. *International journal of cancer* 2000; 85:73-7.
17. Puig P, Urgell E, Capella G, et al. Improved detection of K-ras codon 12 mutations in faecalexfoliated cells. *Laboratory investigation; a journal of technical methods and pathology* 1999; 79:617-8.
18. Herman J G, Graff J R, Myohanen S, et al. Methylation-specific PCR: a novel PCR assay for methylation status of CpG islands. *Proceedings of the National Academy of Sciences of the United States of America* 1996; 93:9821-6.
19. Herman J G, Umar A, Polyak K, et al. Incidence and functional consequences of hMLH1 promoter hypermethylation in colorectal carcinoma. *Proceedings of the National Academy of Sciences of the United States of America* 1998; 95:6870-5.
20. Esteller M, Sparks A, Toyota M, et al. Analysis of adenomatous polyposis coli promoter hypermethylation in human cancer. *Cancer research* 2000; 60:4366-71.
21. Esteller M, Avizienyte E, Corn P G, et al. Epigenetic inactivation of LKB1 in primary tumors associated with the Peutz-Jeghers syndrome. *Oncogene* 2000; 19:164-8.
22. Frigola J, Song J, Stirzaker C, et al. Epigenetic remodeling in colorectal cancer results in coordinate gene suppression across an entire chromosome band. *Nature genetics* 2006; 38:540-9.
23. Osborn N K, Ahlquist D A. Stool screening for colorectal cancer: molecular approaches. *Gastroenterology* 2005; 128:192-206.
24. Song K, Fendrick A M, Ladabaum U. FaecalDNA testing compared with conventional colorectal cancer screening methods: a decision analysis. *Gastroenterology* 2004; 126:1270-9.
25. Ahlquist D A, Shuber A P. Stool screening for colorectal cancer: evolution from occult blood to molecular markers. *Clinica chimica acta; international journal of clinical chemistry* 2002; 315:157-68.
26. Traverso G, Shuber A, Olsson L, et al. Detection of proximal colorectal cancers through analysis of faecal DNA. *Lancet* 2002; 359:403-4.
27. Brenner D E, Rennert G. FaecalDNA biomarkers for the detection of colorectal neoplasia: attractive, but is it feasible? *Journal of the National Cancer Institute* 2005; 97:1107-9.
28. Ahlquist D A, Skoletsky J E, Boynton K A, et al. Colorectal cancer screening by detection of altered human DNA in stool: feasibility of a multitarget assay panel. *Gastroenterology* 2000; 119:1219-27.
29. Imperiale T F, Ransohoff D F, Itzkowitz S H, et al. FaecalDNA versus faecaloccult blood for colorectal-cancer screening in an average-risk population. *The New England journal of medicine* 2004; 351:2704-14.
30. Whitney D, Skoletsky J, Moore K, et al. Enhanced retrieval of DNA from human faecalsamples results in improved performance of colorectal cancer screening test. *J Mol Diagn* 2004; 6:386-95.
31. Loktionov A, O'Neill I K, Silvester K R, et al. Quantitation of DNA from exfoliated colonocytes isolated from human stool surface as a novel noninvasive screening test for colorectal cancer. *Clin Cancer Res* 1998; 4:337-42.
32. Sidransky D, Tokino T, Hamilton S R, et al. Identification of ras oncogene mutations in the stool of patients with curable colorectal tumors. *Science* (New York, N.Y. 1992; 256:102-5.
33. Eguchi S, Kohara N, Komuta K, et al. Mutations of the p53 gene in the stool of patients with resectable colorectal cancer. *Cancer* 1996; 77:1707-10.
34. Esteller M. Epigenetics in cancer. *The New England journal of medicine* 2008; 358:1148-59.
35. Zou H, Harrington J J, Shire A M, et al. Highly methylated genes in colorectal neoplasia: implications for screening. *Cancer Epidemiol Biomarkers Prev* 2007; 16:2686-96.
36. Zitt M, Zitt M, Muller H M. DNA methylation in colorectal cancer—impact on screening and therapy monitoring modalities? *Disease markers* 2007; 23:51-71.

37. Leung W K, To K F, Man E P, et al. Quantitative detection of promoter hypermethylation in multiple genes in the serum of patients with colorectal cancer. *Am J Gastroenterol* 2005; 100:2274-9.
38. Nakayama G, Hibi K, Kodera Y, et al. P16 methylation in serum as a potential marker for the malignancy of colorectal carcinoma. *Anticancer Res* 2007; 27:3367-70.
39. Zou H Z, Yu B M, Wang Z W, et al. Detection of aberrant p16 methylation in the serum of colorectal cancer patients. *Clin Cancer Res* 2002; 8:188-91.
40. Leung W K, To K F, Man E P, et al. Detection of hypermethylated DNA or cyclooxygenase-2 messenger RNA in faecalsamples of patients with colorectal cancer or polyps. *The American journal of gastroenterology* 2007; 102:1070-6.
41. Cottrell S E, Laird P W. Sensitive detection of DNA methylation. *Annals of the New York Academy of Sciences* 2003; 983:120-30.
42. Mikeska T, Bock C, El-Maarri O, et al. Optimization of quantitative MGMT promoter methylation analysis using pyrosequencing and combined bisulfite restriction analysis. *J Mol Diagn* 2007; 9:368-81.
43. Kristensen L S, Mikeska T, Krypuy M, et al. Sensitive Melting Analysis after Real Time-Methylation Specific PCR (SMART-MSP): high-throughput and probe-free quantitative DNA methylation detection. *Nucleic acids research* 2008; 36:e42.
44. Lieberman D A, Weiss D G, Bond J H, et al. Use of colonoscopy to screen asymptomatic adults for colorectal cancer. Veterans Affairs Cooperative Study Group 380. *The New England journal of medicine* 2000; 343:162-8.
45. Imperiale T F, Wagner D R, Lin C Y, et al. Risk of advanced proximal neoplasms in asymptomatic adults according to the distal colorectal findings. *The New England journal of medicine* 2000; 343:169-74.
46. Ore L, Hagoel L, Lavi I, et al. Screening with faecal occult blood test (FOBT) for colorectal cancer: assessment of two methods that attempt to improve compliance. *Eur J Cancer Prev* 2001; 10:251-6.
47. Shields H M, Weiner M S, Henry D R, et al. Factors that influence the decision to do an adequate evaluation of a patient with a positive stool for occult blood. *The American journal of gastroenterology* 2001; 96:196-203.
48. Markovitz Sanford, D (UNIV CASE WESTERN RESERVE) Methods and compositions for detecting cancers. EP1551437, Jul. 13, 2005. App. 20030757461, Jun. 5, 2003.
49. Hoon Dave S B et al. (WAYNE JOHN CANCER INST). DNA Markers for management of Cancer. WO2004086949, Oct. 14, 2004.
50. Lofton-Day Cathy et al. (EPIGENOMICS AG; LOFTON-DAY CATHY). Methods and nucleic acids for the analysis of colon cell proliferative disorders. WO2005001140, Jan. 6, 2005.
51. Todd Alison Velyian et al. (Johnson & Johnson Res Pty LTD). Method for detection of alkylated cytosine in DNA. EP1644519, Apr. 12, 2006. Appl. 20040737521, Jul. 5, 2004.
52. Lofton-Day Cathy et al. (EPIGENOMICS AG; LOFTON-DAY CATHY; EBERT MATHIAS). Methods and nucleic acids for the detection of metastasis of colon cell proliferative disorders. WO 2006002344, Jan. 5, 2006.
53. Shuber Anthony P. Methods for detecting hypermethylated nucleic acid in heterogeneous biological samples. US6818404, May 8, 2003. Appl. US20020123071, Apr. 11, 2002.

The invention claimed is:

1. In vitro method for the diagnosis of colorectal cancer comprising:
   A. obtaining a biological sample of colon cells from a human being; and
   B. determining from the biological sample a promoter methylation status of APC, RARB2 p14, p16 and MGMT genes, wherein an increase in the methylation of a plurality of promoter regions of said genes as compared to that in a control sample is indicative of colorectal cancer.

2. The in vitro method according to claim 1, characterised in that the biological sample is taken from a stool sample.

3. The in vitro method according to claim 1, characterised in that the determination of methylation is carried out on fecal DNA.

4. The in vitro method according to claim 1, 2 or 3, characterised in that the determination of methylation is carried out by melting curve analysis.

* * * * *